(12) United States Patent
Isaacson et al.

(10) Patent No.: US 12,311,128 B2
(45) Date of Patent: May 27, 2025

(54) NEEDLE AND CATHETER INSERTION DEVICE

(71) Applicant: Becton, Dickinson and Company, Franklin Lakes, NJ (US)

(72) Inventors: Shawn Ray Isaacson, Layton, UT (US); Weston Finch Harding, Lehi, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 827 days.

(21) Appl. No.: 16/054,552

(22) Filed: Aug. 3, 2018

(65) Prior Publication Data

US 2019/0038876 A1 Feb. 7, 2019

Related U.S. Application Data

(60) Provisional application No. 62/541,205, filed on Aug. 4, 2017.

(51) Int. Cl.
*A61M 25/06* (2006.01)
*A61B 17/34* (2006.01)
*A61M 5/32* (2006.01)

(52) U.S. Cl.
CPC ....... *A61M 25/065* (2013.01); *A61B 17/3415* (2013.01); *A61M 5/3286* (2013.01);
(Continued)

(58) Field of Classification Search
CPC ................ A61M 5/3286; A61M 25/06; A61M 25/0606; A61M 25/065; A61M 25/0693;
(Continued)

(56) References Cited

U.S. PATENT DOCUMENTS 2,697,438 A 12/1954 Hickey
3,090,384 A * 5/1963 Baldwin ............. A61M 5/3286
604/272

(Continued)

FOREIGN PATENT DOCUMENTS

JP H05-502402 A 4/1993
JP 2006-514874 A 5/2006
(Continued)

OTHER PUBLICATIONS

International Search Report and Written Opinion of the International Searching Authority dated Jan. 8, 2019, which issued in the corresponding PCT Application No. PCT/US2018/045108.

*Primary Examiner* — Kevin C Sirmons
*Assistant Examiner* — Leah J Swanson
(74) *Attorney, Agent, or Firm* — Dickinson Wright PLLC

(57) ABSTRACT

A needle is provided that can be used for introducing or aspirating fluids to a patient or as an introducer needle for positioning and inserting a catheter, such as a peripheral IV catheter into a patient. The needle can be an introducer needle that extends from the distal end of the catheter during insertion. The needle has an insertion tip with a configuration to assist penetration into a vein with a reduced incidence of injuring the inner surface of the vein or inadvertently passing through side wall of the vein. The needle tip can be farmed with a curved distal end surface where the pointed tip is spaced radially inward relative to the outer surface of the needle. In another embodiment the needle tip can have a reverse beveled surface having an axial length, angle, and curvature to assist in penetrating the vein with a reduced incidence of transfixing the vein.

6 Claims, 12 Drawing Sheets

(52) U.S. Cl.
CPC ...... *A61B 17/3478* (2013.01); *A61M 25/0606* (2013.01); *A61M 25/0618* (2013.01); *A61M 25/0693* (2013.01)

(58) Field of Classification Search
CPC .......... A61M 25/0618; A61M 25/0643; A61B 5/150396; A61B 17/3415; A61B 17/3478
See application file for complete search history.

(56) References Cited

U.S. PATENT DOCUMENTS

| | | | |
|---|---|---|---|
| 3,308,822 A * | 3/1967 | De Luca | A61M 5/3286 604/274 |
| 4,525,157 A | 6/1985 | Vaillancourt | |
| 4,850,960 A | 7/1989 | Grayzel | |
| 4,894,052 A | 1/1990 | Crawford | |
| 5,515,871 A * | 5/1996 | Bittner | A61M 5/3286 128/898 |
| 5,968,022 A * | 10/1999 | Saito | B24B 19/16 604/264 |
| 6,156,010 A | 12/2000 | Kuracina | |
| 6,440,119 B1 | 8/2002 | Nakada et al. | |
| 8,603,037 B1 | 12/2013 | Wiley et al. | |
| 9,597,461 B2 | 3/2017 | Aasmul | |
| 2002/0052580 A1 | 5/2002 | Ooyauchi | |
| 2006/0276759 A1* | 12/2006 | Kinast | A61M 5/3286 604/272 |
| 2007/0233007 A1 | 10/2007 | Adams | |
| 2010/0016786 A1 | 1/2010 | Drews et al. | |
| 2010/0137804 A1* | 6/2010 | Wiley | A61M 25/0067 604/168.01 |
| 2011/0208215 A1 | 8/2011 | Modesitt et al. | |
| 2011/0295152 A1* | 12/2011 | Sasaki | A61B 5/150259 600/573 |
| 2014/0107569 A1 | 4/2014 | Fischer et al. | |
| 2016/0045715 A1 | 2/2016 | Galgano et al. | |
| 2016/0256667 A1 | 9/2016 | Ribelin et al. | |
| 2016/0338734 A1* | 11/2016 | Shah | A61B 5/14503 |
| 2018/0153579 A1* | 6/2018 | Ueda | A61M 5/32 |

FOREIGN PATENT DOCUMENTS

| | | |
|---|---|---|
| WO | 9205816 A1 | 4/1992 |
| WO | WO-2016094620 A1 | 6/2016 |
| WO | 2017/074677 A1 | 5/2017 |

\* cited by examiner

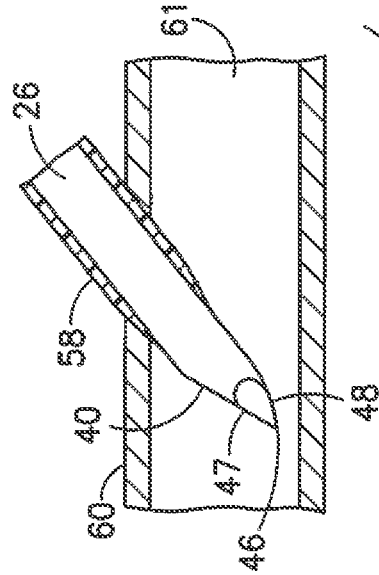
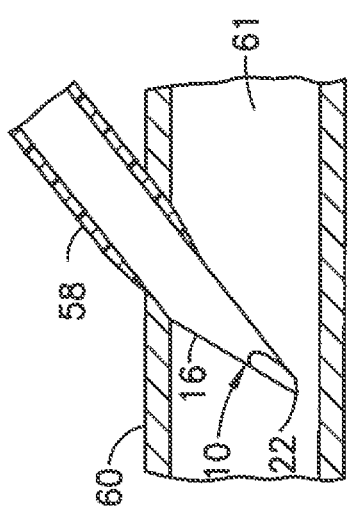
FIG. 4
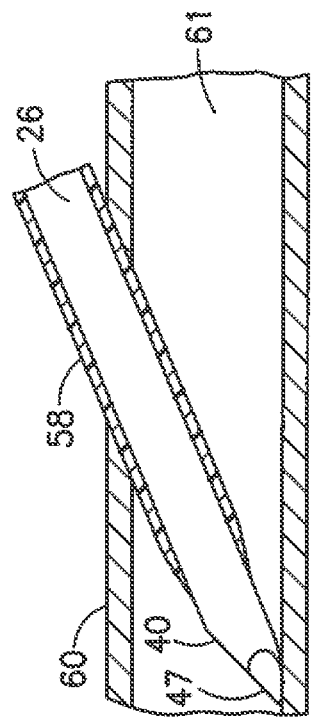
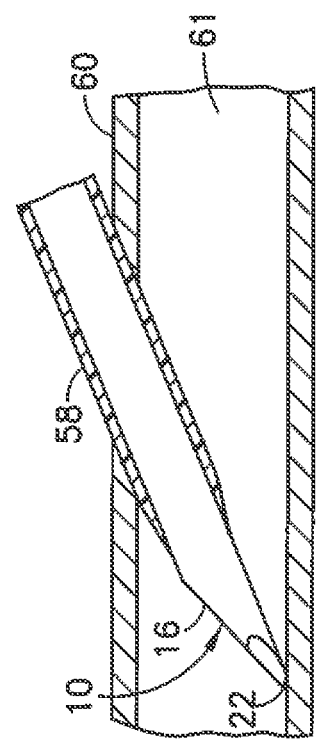
FIG. 5

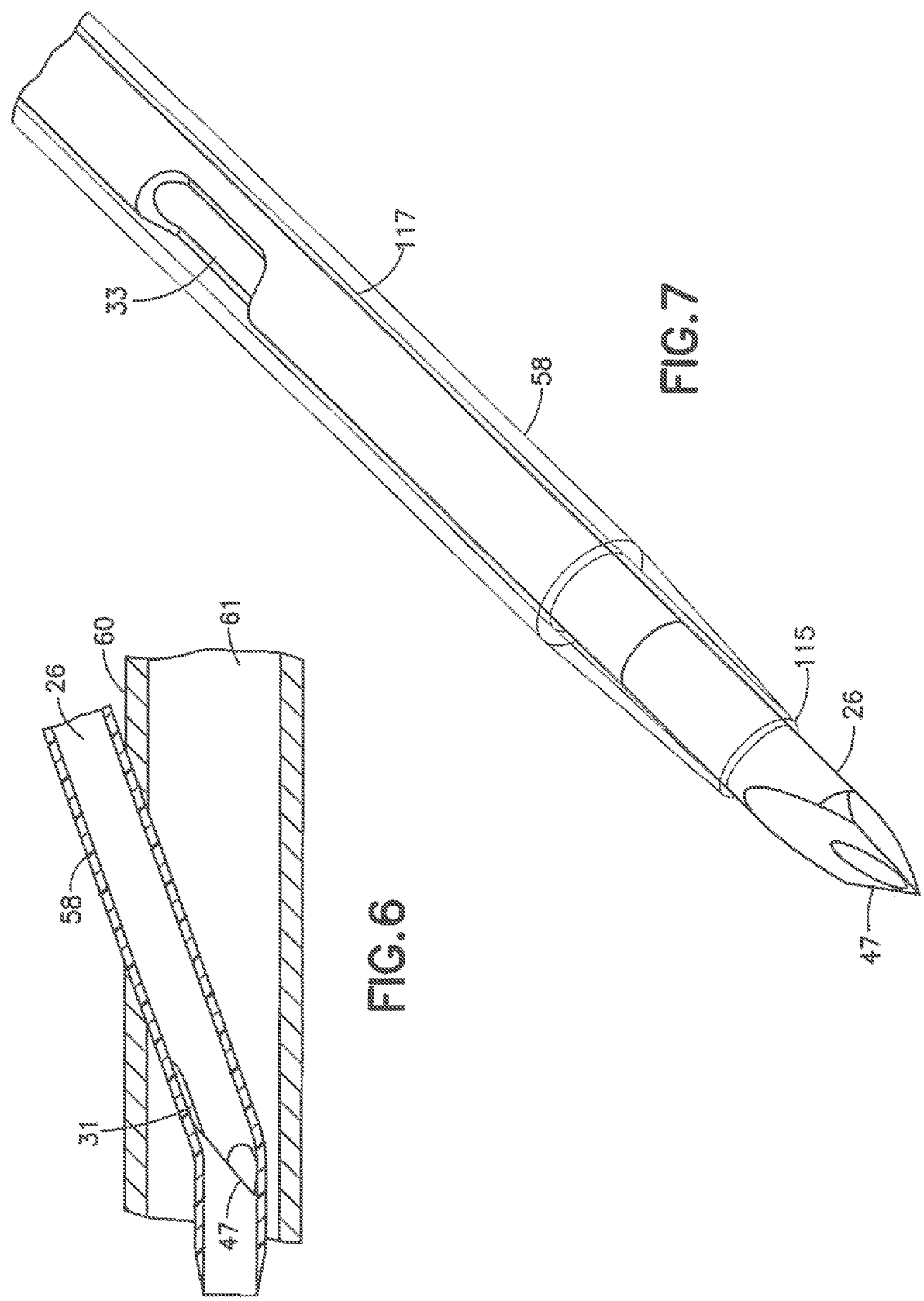

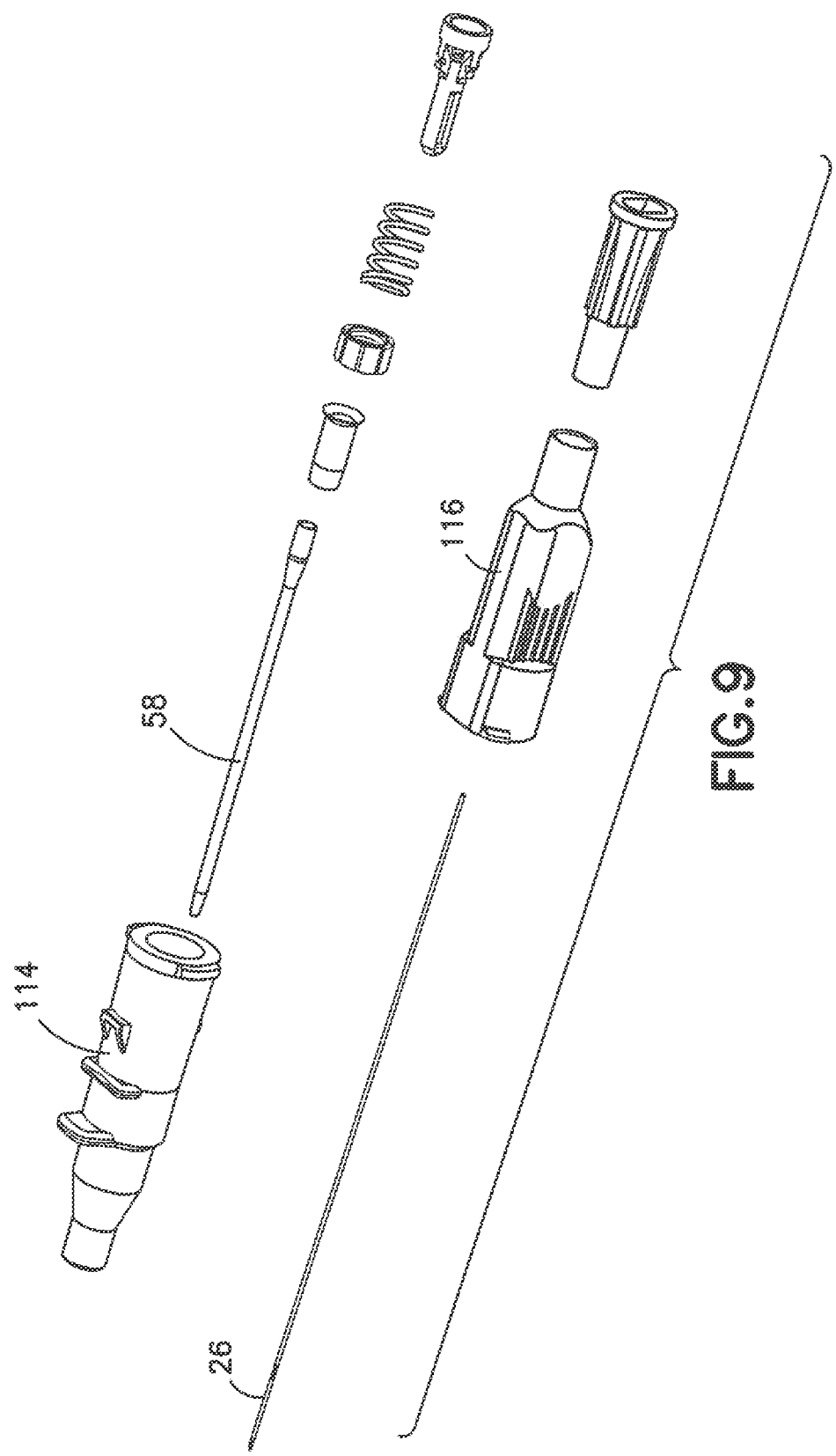

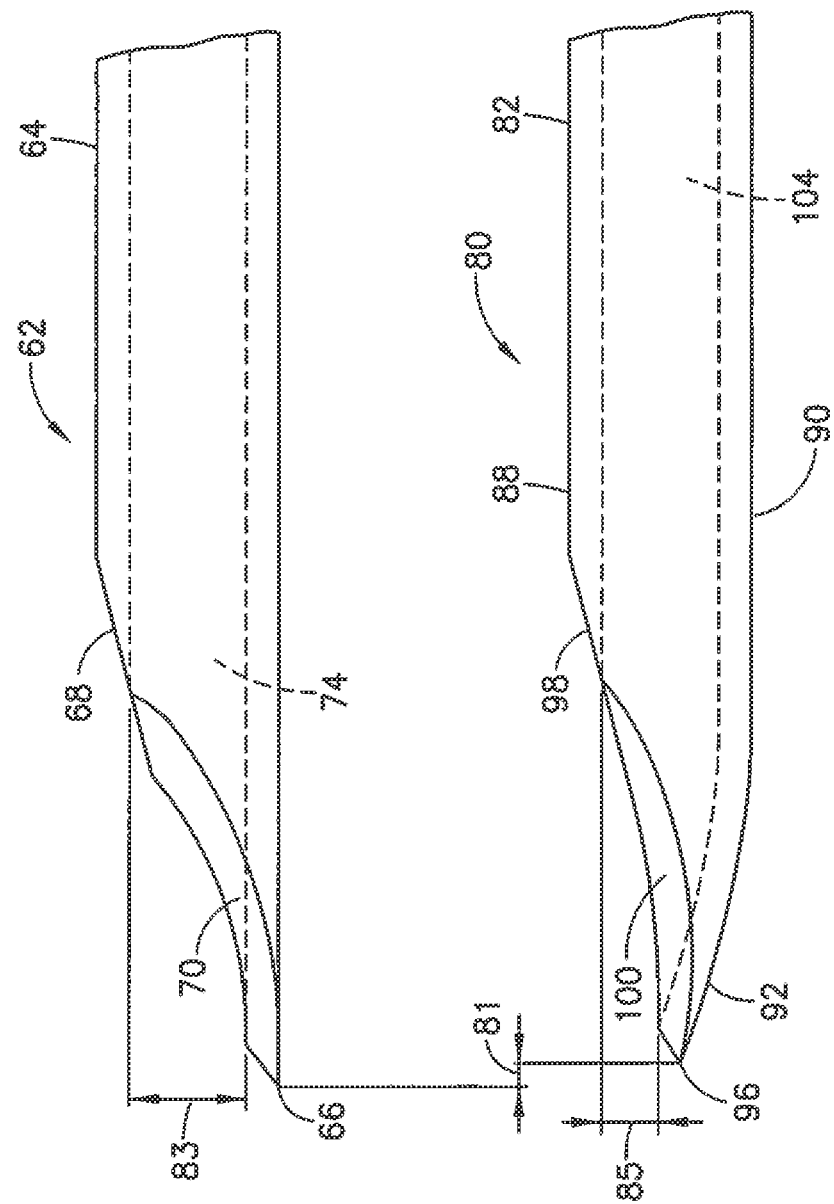

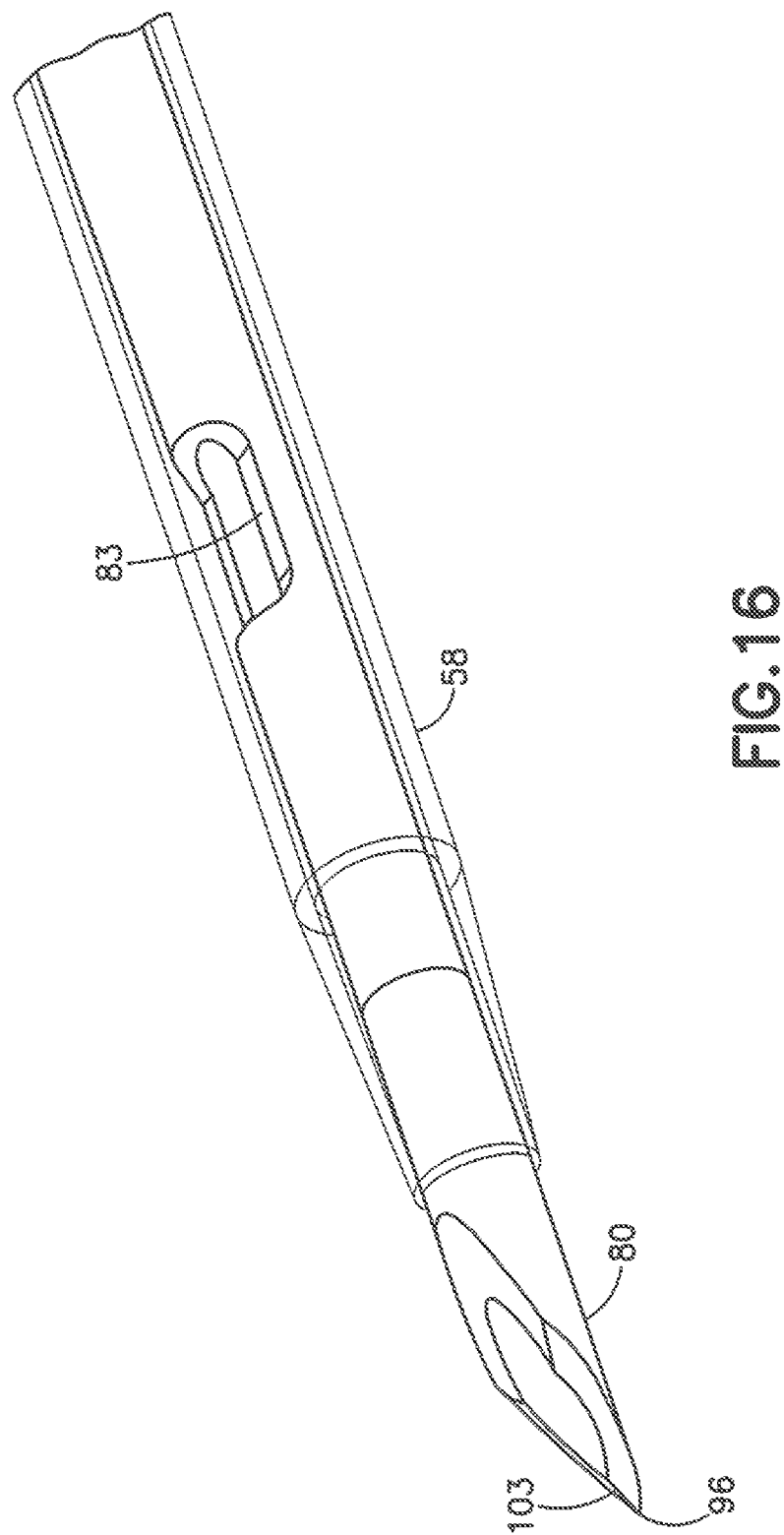

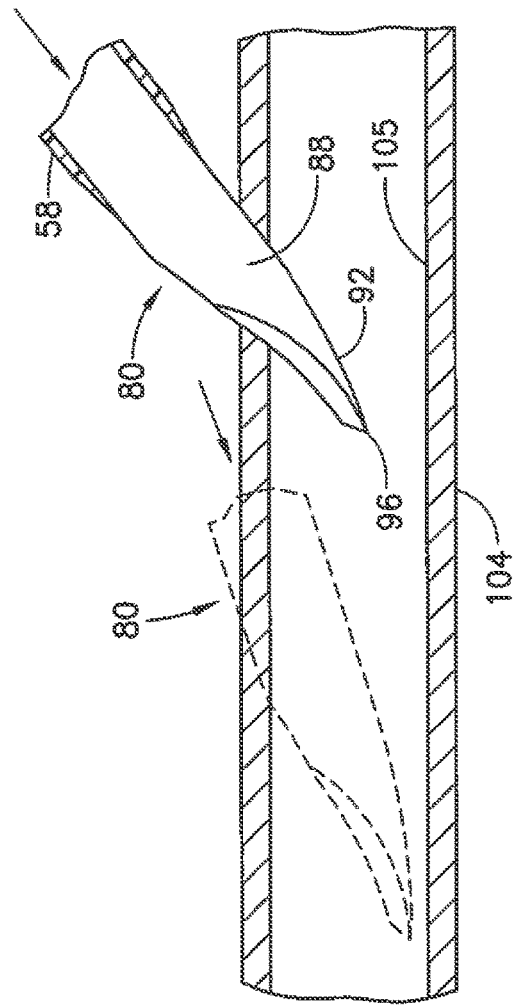
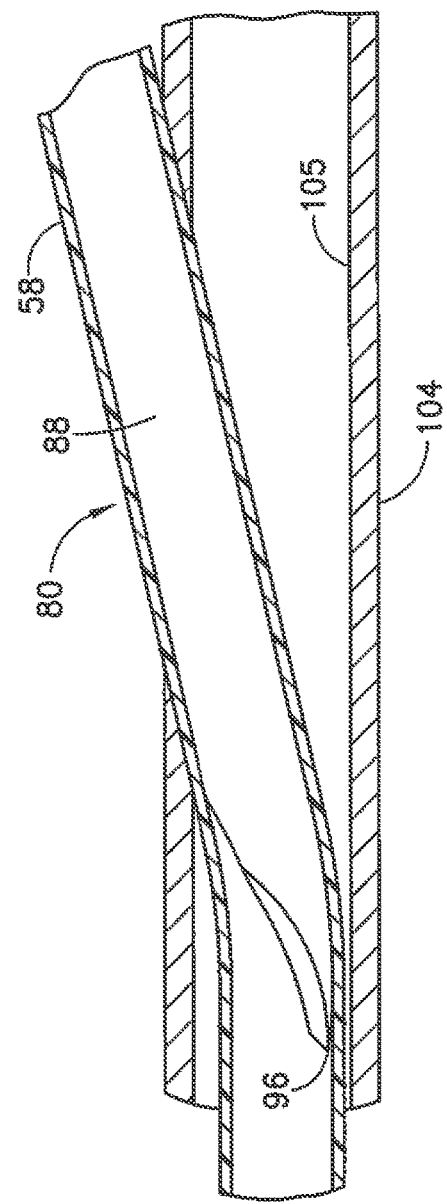

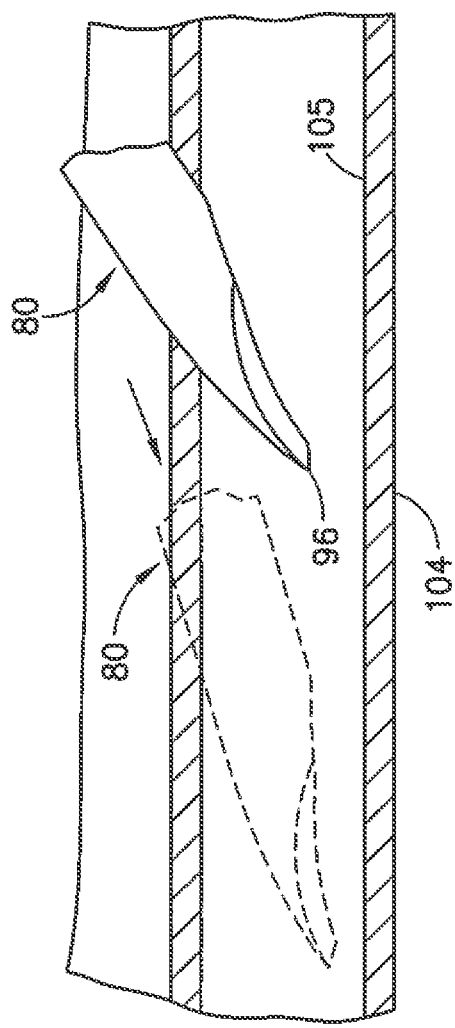
FIG. 19
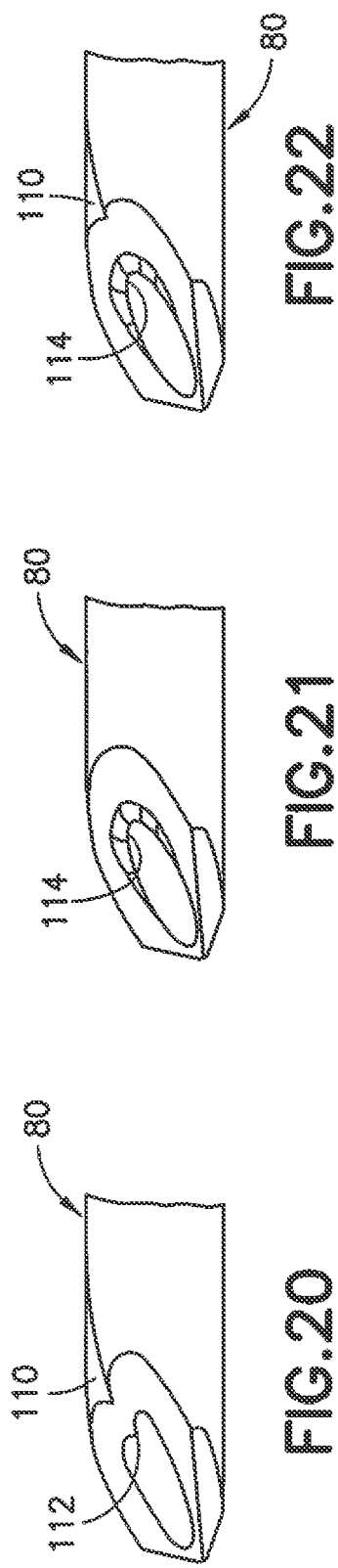
FIG. 20
FIG. 21
FIG. 22

NEEDLE AND CATHETER INSERTION DEVICE

This application claims priority to U.S. provisional application Ser. No. 62/541,205 filed on Aug. 4, 2017, which is hereby incorporated by reference in its entirety.

BACKGROUND OF THE INVENTION

Field of the Invention

The invention is in the field of needles, introducer needles for catheter placement, catheter insertion devices, and a method of introducing a needle and/or introducing a guide wire into a patient where the needle or guide wire has a tip with a shape and configuration to assist in the insertion into a vein or artery with a reduced incidence of transfixing the vein or artery by inhibiting passing through or damaging the inner surface of the vein or artery. The invention is also directed to a method of introducing a needle into a patient with an improved ease of insertion and positioning a catheter device in a vein for delivering a medication or drug to a patient. In one embodiment, the invention is directed to a catheter insertion device that can be operated in a manner to improve the efficiency of catheter insertion into a patient while avoiding the need for repeated attempts for proper placement.

Description of the Related Art

Catheters are generally used for parenteral nutrition. IV fluid replacement and for administering analgesics and antibiotics. Catheters can be inserted at the bedside using sterile techniques and can remain in place for several weeks. The insertion (venipuncture) is performed above and below the antecubital fossa in the cephalic, basilic, or brachial veins. The catheter tip can be introduced into the vein and be advanced the full length of the catheter.

Inserting and properly positioning an IV catheter on the first attempt generally requires a level of skill that that is not possessed by some clinicians. The accurate placement of a catheter and the insertion device in the vein on the first attempt is a great advantage to reduce the incidence of damage to the vein and/or the surrounding tissue. Proper placement of the catheter and the insertion needle is important to minimize the discomfort and pain to the patient as well as reducing damage or injury to the vein. Damage caused to the vein during insertion and placement of the catheter can cause accelerated clotting and thrombosis.

Some advantages of certain catheters are the reduced frequency of repeated venipunctures for labs/restarts, decreased incidence of catheter related infections, extended implant/indwell duration, improved clinical outcomes, patient satisfaction and associated cost savings. Placing the catheter tip in the larger diameter veins in the upper arm compared to the smaller veins provide improves drug delivery therapy and hemodilution. Catheters can be used for infusing contract media at higher flow rates that are typically done by CV catheters such as PICC applications.

Certain prior catheter devices can include an integral guidewire that is advanced through the lumen of a needle and into the vein after the needle accesses the vein. Often an ultrasonic probe or imaging device is used to locate the needle in the desired location. The catheter is then advanced over the guidewire into the vein. The needle and guidewire are then detached and separated from the catheter which remains in place in the vein.

The introducer needle or other insertion device typically requires a sharp tip to pierce the skin and the vein of the patient with minimal resistance to minimize the pain to the patient. The introducer needle is generally placed at a steep inclined angle with respect to the surface of the skin and the longitudinal dimension of the vein to be pierced to allow penetration through the skin and the wall of the vein. After the tip of the introducer needle pierces the wall the vein, the angle of the insertion is lowered to be able to slide the needle and catheter into the vein a distance sufficient to properly position the catheter in the vein. The initial steep angle of insertion can result in the sharp tip of the needle or insertion device piercing or damaging the inner surface of the wall of the vein at a location opposite the point of entry.

While the prior devices are generally suitable for the intended use, there is a continuing need for improved devices and methods for introducing the devices for controlling the penetration of a needle or cannula for delivering a drug or medicament. In particular there is a need for an insertion device that is able to effectively pierce the skin and the vein while reducing the risk of injury or damage to the vein.

SUMMARY

The present invention is directed to a needle for placement in a selected location in the vein of a patient with reduced risk of transfixing the needle or a guide wire through the wall of the vein. The invention is also directed to a catheter insertion device.

In one embodiment, the invention is can be, a needle for introducing and withdrawing fluid from a patient, or an introducer or insertion needle for a medical device such as catheter for insertion and placement of the catheter in the vein or artery of the patient. The insertion device is able to place the catheter in a selected location with reduced risk of injuring the inner surface of the vein during the process and a more reliable placement in the vein. The needle can be used with a guide wire for inserting the guide wire into the patient for advancing a catheter, such as a IV catheter or PICC catheter. In other embodiments, the needle can be solid core needle. The needle and insertion device have a configuration with cutting edges to reduce the pain and discomfort to the patient during insertion.

The invention is also directed to a needle having a body with a needle tip geometry to inhibit transfixing when inserted into a vein. In one embodiment, the needle tip geometry can be used on a Blood Draw Phlebotomy needle for withdrawing blood through a lumen of a needle into a vacuum tube. The needle tip geometry can also be used for other procedures where it is desired to reduce the needle bending caused by a long bevel needle.

A feature of the invention is to provide a needle having a configuration that is effective in piercing the skin and the vein such as during the insertion of a catheter and to reduce or minimize the risk of piercing or damaging the inner surface of the vein after the needle enters the lumen of the vein. The needle of the invention is configured to assist in positioning the needle at an initial angle with respect to the surface of the skin and the longitudinal dimension of the vein during the insertion into the vein to reduce the risk of damaging the inner surface of the vein that can otherwise be caused by the sharp distal tip of the needle. In other embodiments, the needle tip geometry can used with a guide wire for positioning a catheter in a patient.

One feature of the invention is to provide a needle having a distal tip to reduce the occurrence of transfixing the vein or artery during insertion. The needle can be a cannula for introducing fluids to the patient, withdrawing fluids or aspirating fluid from the patient or can be used as an introducer needle for a catheter. The needle can be used for the aspiration of blood, spinal fluid, or other fluids from a patient. The needle can be a solid needle or can include a lumen. In the embodiment where the needle is an introducer needle for a catheter, the needle can include an opening, such as a groove, to provide flashback of blood when the needle penetrates the vein or artery to provide an indication that the needle tip is positioned in the lumen of the vein.

The needle of the invention includes a distal tip with a sharp point or tip for penetrating the skin and penetrating the vein or artery of a patient where the distal tip has a shape and configuration to minimize the risk of the sharp point from transfixing, penetrating, or injuring the inner surface of the vein or artery during penetration. The needle has a configuration so that the trajectory of the needle will promote a flattening of the needle after insertion to a lower angle with respect to the longitudinal direction of the vein or artery to reduce the risk of transfixing or injuring the inner surface of the vein at a location opposite the insertion site of the needle.

The catheter insertion device in one embodiment includes a distal tip with a configuration that is able to penetrate the skin and vein or artery with minimal discomfort to the patient and effectively position a catheter in the vein or artery. The distal tip is able to easily penetrate the vein or artery at a suitable angle where the sharp tip avoids direct contact with the inner surface of the vein or artery at a location opposite the insertion site or point of penetration by the sharp tip.

The introducer needle of the insertion device in one embodiment includes a body having a longitudinal dimension with a proximal end and a distal end. The body in one embodiment can have a substantially cylindrical shape that can be solid or hollow to define a lumen or passage through the needle. The body has a first longitudinal side surface and a second longitudinal side surface opposite the first longitudinal side surface and a bevel extending from the second longitudinal side surface at an inclined angle toward the first longitudinal side surface. The second longitudinal side surface has a distal end with a curved surface extending in the longitudinal direction from an outer peripheral surface to a distal tip toward a center axis of the needle. A catheter is positioned on the needle that can slide over the tip of the needle with little or minimal interference from the sharp needle tip. The needle can be used with a guide wire that can be passed through the lumen of the needle to guide the catheter into the vein.

The introducer needle of the invention includes a distal tip configured to penetrate the vein or artery where the distal tip has a curved surface oriented to face the opposing wall of the vein opposite the point of penetration of the vein. The curved surface is oriented so that contact of the curved surface with the inner surface of the vein or artery occurs rather than the sharp distal tip to reduce the damage or penetration to the inner surface of the vein or artery during insertion. The curved surface promotes the flattening of the angle of the needle to assist in inserting the needle in a direction substantially parallel to the longitudinal dimension of the vein or artery. The curved surface provides a more optimal path for the catheter to follow for advancing the catheter from the needle over the bevel and sharp tip. The curved surface enables the catheter to bend easily in the longitudinal direction of the vein, thus easing the advancement and reducing trauma to the vein from the edge of the catheter tip on the inner wall of the vein.

The needle according to one aspect of the invention includes a distal tip formed by a first beveled surface extending from a peripheral outer surface of the body toward the distal tip. A second reverse beveled surface and a third reverse beveled surface are formed on the body to converge to the distal tip and form a longitudinally extending cutting edge between the second and third beveled surfaces. In one embodiment, the cutting edge can have a curved, convex profile that curves toward the distal tip.

The various aspects and features of the invention are attained by providing a needle, such as an introducer needle, where a distal end of the needle has a curved surface that converges toward a distal tip and where the distal end includes at least one beveled surface that is spaced from the curved surface toward the distal tip.

The features of the invention are further attained by providing a needle where the body of the needle has a lumen forming an axial passage that has an inner diameter less than a standard needle to provide a greater axial surface area of the distal end that penetrates a vein or artery. The distal tip includes at least one beveled surface forming a cutting edge having a shorter axial length than a standard needle with a similar length of the cutting edges as a standard needle.

The features of the invention are further provided by an introducer needle having a body with a longitudinal dimension with a proximal end and a distal end, a first longitudinal side and a second longitudinal side opposite the first longitudinal side. The second longitudinal side has a distal end that curves toward the center axis of the body and terminates at a distal tip. A first beveled surface extends from the first longitudinal side surface toward the distal end. A second beveled surface and a third beveled surface are formed and extend from a distal end of the first beveled surface to the distal tip.

The various features of the invention are further attained by providing a method of inserting a needle into a patient by use of the introducer needle having a distal tip with a beveled surface on a first side and a curved surface on a second side. The needle is oriented with the curved side facing the skin of the patient and the beveled surface facing away from the skin. The needle penetrates the skin and vein or artery of the patient so that the curved surface of the distal tip faces the inner wall of the vein or artery on a side opposite the point of penetration to reduce the occurrence of the distal tip penetrating the inner surface of the vein or artery.

It will be understood that each of the preferred or optional features of the various embodiments may be combined with other features and features described in combination with one or more particular features may also be combined with one or more other features of the other embodiments.

These and other features of the invention will become apparent from the following detailed description of the invention, which in conjunction with the drawings disclose various embodiments of the invention.

BRIEF DESCRIPTION OF THE DRAWINGS

The following is a brief description of the drawings in which:

FIG. 4 is a side view showing the angle of initial penetration of the needles into the patient;

FIG. 5 is a side view showing the reduced angle of penetration of the needles after piercing the vein;

FIG. 6 is a side view showing the needle and catheter of the invention positioned in the vein;

FIG. 7 is a perspective view of the needle showing the notch providing the blood flashback;

FIG. 9 is an exploded view of the catheter assembly of FIG. 8;

FIG. 15 is a side view comparing the length of the beveled surfaces of the needle of FIG. 13 in relation to the standard needle of FIG. 7;

FIG. 16 is perspective view of the needle showing the notch for the blood flashback;

FIG. 17 is a side view showing the initial insertion angle of the needle of FIG. 13 and FIG. 13 during insertion into the patient;

FIG. 18 is a side view showing the reduced angle of the needle of FIG. 13 after the initial penetration of the vein;

FIG. 19 is a side view showing a method of inserting the needle into the patient according to a timber embodiment;

FIG. 20 is a perspective view of the needle in a further embodiment of the invention;

FIG. 21 is a perspective view of the needle in another embodiment of the invention; and FIG. 22 is a perspective view of the needle in further embodiment of the invention.

DETAILED DESCRIPTION

A needle, such as a catheter introducer needle, is provided for positioning a catheter in a patient for delivering a medication or other substance to a patient or for use with a guide wire to introduce the guide wire into the patient for advancing a catheter. The terms "needle" and "cannula" can be used herein interchangeably to refer to a member having a sharpened or beveled end for insertion into an injection or insertion site on a subject. In one embodiment, the needle can be a thin hollow tubular member. In other embodiments, the needle can be a solid member. As used herein, the "distal" direction is in the direction toward the patient and injection site, and the "proximal" direction is the opposite direction. "Axial" means along or parallel to the longitudinal axis of the needle or other member and the "radial" direction is a direction perpendicular to the axial direction.

The invention is directed to a needle or cannula that can be used alone for introducing a substance to a patient, aspirating a substance from a patient, or can be used with a catheter for inserting and positioning the catheter into the vein or artery of a patient. In other embodiments, a guide wire can extend through the lumen of the needle for guiding a catheter in to the vein or artery. In the illustrated embodiments, the needle is used with a catheter for positioning the catheter in the vein of the patient although the needle is not limited to use with a catheter. The needle can include a lumen for delivering a substance or providing flashback when the vein or artery is pierced. In other embodiments the needle can be a solid body with or without a flashback feature.

Figure 1:
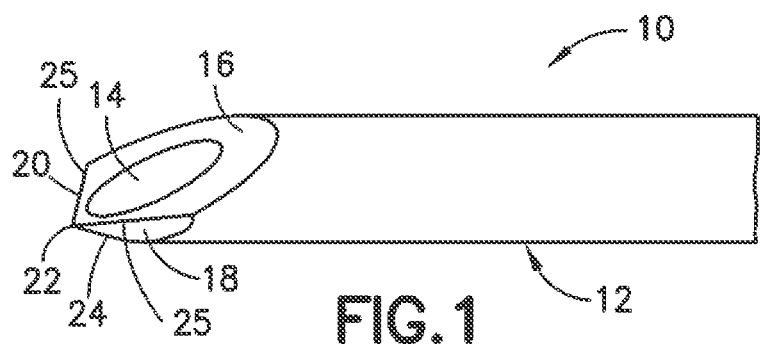
FIG. 1 is a perspective view of a needle commonly used to insert and position a catheter in a patient showing the reverse beveled surfaces that form the sharp tip.

In the embodiments described, the needle can be a suitable gauge with a lumen having an appropriate diameter for delivering or aspirating the intended fluid in the patient. In embodiments described, the needle can be 18 to 26 gauge. In one embodiment, the needle can be 20 to 22 gauge. Referring to the drawings, a needle 10 is shown in FIG. 1 having a body 12 and lumen 14. A bevel 16 is formed providing a major surface at an inclined angle relative to the longitudinal dimension of the body 12 and extends from an outer edge of the body across the diameter of the body 12. A second reverse bevel 18 and a third reverse bevel 20 are formed opposite the bevel 16. The reverse bevel 18 and reverse bevel 20 are formed at an incline to each other and converge with the bevel 16 to form a sharp tip 22 and an angled cutting edge 24 extending between the second reverse bevel 18 and third reverse bevel 20 and at an incline opposite the bevel 16. In the embodiment shown in FIG. 1, the bevels 18 and 20 form a cutting edge 25 having an axial length greater than ½ the longitudinal length of the bevel 16. The cutting edge 24 extends from the tip 22 to the outer peripheral edge of the body 12. As shown, the reverse bevels 18 and 20 and the corresponding cutting edges 25 extend from the tip 22 and terminate at a point below the axial center of the body indicated by line 27 with respect to the second longitudinal side. The bevels 18 and 20 can be formed so that the angle between the cutting surfaces form an angle of about 60° to 70°.

Figure 2:
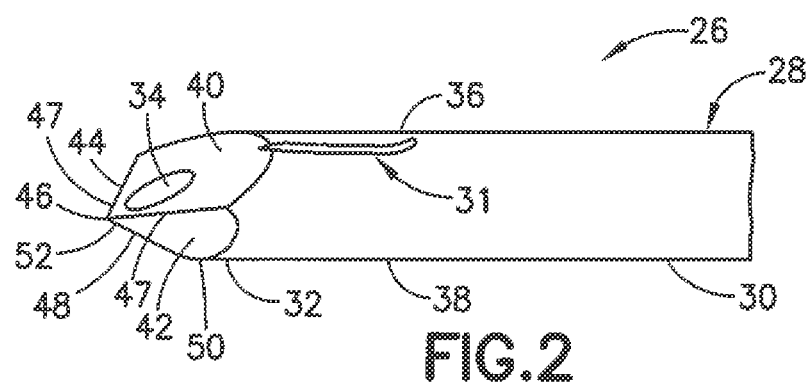
FIG. 2 is a perspective view of the needle in one embodiment of the invention showing the reverse beveled surfaces forming the sharp tip.

FIG. 2 shows an embodiment of the needle where a needle 26 includes a body 28 having a longitudinal dimension with a proximal end 30 and a distal end 32. In the embodiment shown, a lumen 34 extends between proximal end 30 and distal end 32. Typically, the body 28 has a straight, substantially cylindrical shape as shown in the drawings. In the embodiment shown, lumen 34 has an inner diameter of not more than about ⅓ the outer diameter of the outer wall of the body 28. In other embodiments, the lumen 34 can have an inner diameter of about ¼ or less the inner diameter of the needle body. Body 28 in the embodiment shown has a first longitudinal side surface 36 and a second longitudinal side surface 38 opposite first longitudinal side 36. The needle 26 can be, for example, a 20 gauge needle having an outer diameter of about 0.90 mm where the lumen 34 has an inner diameter less than a standard lumen of a 20 gauge needle. By way of example, the needle 26 can have a lumen with an inner diameter of about ¼ or less the outer diameter of the needle.

A groove or recess 31 is provided on the first longitudinal side surface 36 at the distal end of the body 28 to provide a blood flashback passage feature. When the needle 26 penetrates the vein, blood travels through the groove 31 to the inner surface of the catheter where the blood can travel to a location or device where the blood can be visualized by the operator as an indication of placement of the needle and catheter in the vein.

The distal end 32 of body 28 is formed with a first bevel 40 extending at an inclined angle with respect to the longitudinal dimension of body 28 from first longitudinal side surface 36 toward the second side 38 and the distal end 32. The first bevel 40 can have, for example, a bevel angle of about 12-22° with respect to the longitudinal axis of the needle. In other embodiments, the bevel 40 can have a bevel angle of about 12° to 17°. A second reverse bevel 42 and third reverse bevel 44 are famed on the opposite side of the body from the bevel 40 and extend from the second longitudinal side surface 38 and converge with first bevel 40 to form a distal tip 46 and cutting edges 47 between reverse bevels 42 and 44 and first bevel 40. The second reverse bevel 42 and third reverse bevel 44 converge to define a cutting edge 48 at a distal end 52 forming distal tip 46. The second reverse bevel 42 and the third reverse bevel 44 have a bevel angle greater than the bevel angle of bevel 40.

Figure 3:
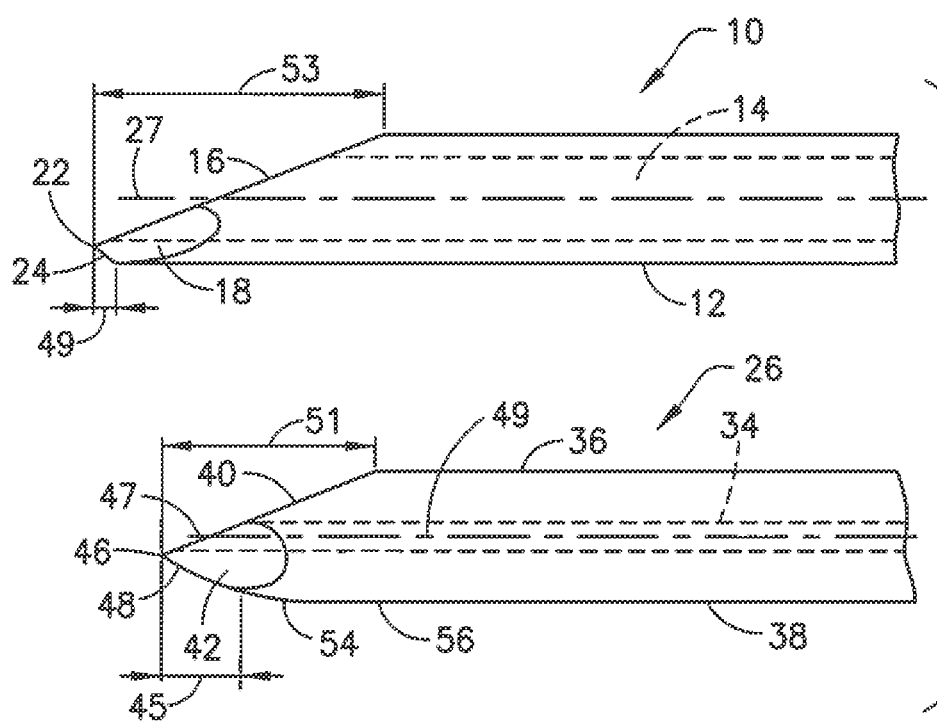
FIG. 3 is a side view comparing the length of the beveled surfaces of the needle according to the invention relative to a standard needle.

In the embodiment shown in FIG. 2 and FIG. 3, the reverse bevels 42 and 44 are spaced radially inward from the outer cylindrical surface of the body 28 and have an axial length to reduce the axial length of the bevel 40 20% to 50% relative the needle 10 where the angle of the bevel 16 and the angle of the bevel 40 are the same. The ratio of the axial length of the bevels 42 and 44 as measured from the tip 46 to the proximal end of the respective bevel to the axial length of the bevel 40 can be about 1:1.5 to about 1:1.8. In one embodiment, the ratio of the axial length of the bevels 42 and 44 with respect to the axial length of the bevel 40 can be about 1:1.6 to about 1:1.7. The cutting edges 47 can be formed at an angle of about 75° to 85°. In one embodiments, the cutting edges are formed at an angle of about 80°.

The cutting edge 48 formed between bevels 42 and 44 has an axial length greater than the axial length of the cutting edge 24 of needle 10. In one embodiment, the ratio of the axial length of the cutting edge 48 to the axial length of the bevel 40 can be about 1:2.5 to about 1:3. In other embodiments, the ratio of the axial length of the cutting edge 45 to the axial length of the bevel 40 is about 1:2.7 to about 1:2.8.

FIG. 3 illustrates a comparison between needle 10 and needle 26 of the present invention. As shown in FIG. 3, second longitudinal side surface 38 of the needle 26 is formed with a curved distal end portion 54 forming a taper that curves inwardly from a peripheral outer surface 56 of body 28 to the proximal end of the cutting edge 48 at distal tip 46. The curved end portion 54 forms a continuous curve extending inwardly from the outer surface 56 of the body 28 toward the axial center of the needle 26. The bevels 42 and 44 have an axial length less than the axial length of the bevel 40 and less than the axial length of the curved end portion 54 so that a proximal end of the curved end portion 54 forms a conical shaped surface that extends between the surface 38 and the cutting edge 48. As shown, the cutting edge 48 is spaced radially inward from the peripheral outer edge or surface of the body 28.

In the embodiment of FIG. 2, lumen 34 has a smaller diameter than the lumen 14 in the embodiment of FIG. 1 to provide a larger surface area for the bevel surface 40 forming the distal face of the needle 26 compared to the surface of the bevel 16 of the needle 10. In one embodiment, second reverse bevel 42 and third reverse bevel 44 can have an axial length less than an axial length of the first bevel 40. The second and third bevels 42 and 44 can have a substantially concave configuration as shown in FIG. 3. By reducing the inner diameter of lumen 34, the larger surface areas of reverse beveled surfaces 42 and 44 compared to the bevels 18 and 20 of the needle 10 of FIG. 1 provide a shorter overall axial length of the distal end portion while maintaining the same or substantially the same length of cutting edges 20 and 47 that pierce and cut the skin and the vein. The axial length of the cutting surface 47 can be about 25% shorter than the cutting edges 20 for the same outer diameter of the needle body and the same bevel angles while increasing the axial length of the cutting edge 48 relative to the axial length of the cutting edge 24. In one embodiment, cutting edges 47 have an axial length of about ⅓ to about ½ the axial length of first bevel 40. In one embodiment, the ratio of the axial length of cutting edges 47 to the axial length of first bevel 40 is about 1:2.5. The wider angle between the cutting edges 47 provide a shorter axial cutting length relative to the longitudinal dimension of the needle 26. The shorter axial length of the cutting surfaces provides a faster cut through the skin with a predetermined insertion rate that can reduce the cutting time and the perceived pain by the patient.

The lumen 34 in the embodiment of FIGS. 2 and 3 has an inner diameter less than the thickness of the outer wall of the body 26. In one embodiment, the inner diameter of the lumen 34 is about 0.2 to about 0.3 times the outer diameter of the body 28. In other embodiments, the inner diameter of the lumen 34 is about 0.22 to about 0.24 times the outer diameter of the body 28.

As shown in FIG. 3, cutting edge 48 formed between bevels 42 and 44 and the bevel 40 of needle 26 have an axial length indicated by arrow 45 is greater than the corresponding edge 24 of the needle 10 indicated by arrow 49 while forming a distal end portion indicated by arrow 51 with a shorter axial length relative to the axial length of needle 10 indicated by arrow 53. The angles of the beveled surfaces are substantially the same while the axial length of first beveled surface 40 is shorter than bevel 16 of the needle 10 of FIG. 1 and reverse bevels 42 and 44 of needle 26 have an axial length greater than axial length of bevels 18 and 20 of the needle 10 thereby forming a distal end with a shorter axial length relative to the needle 10. As shown in FIG. 3, second longitudinal side surface 38 has a rounded, curved profile 54 at the distal end that converges at the distal tip 46. The shorter axial length of the distal end of the needle defined by the beveled surfaces while maximizing the total length of the cutting edges provides improved comfort and reduced perceived pain by the patient compared to longer cutting edges. In one embodiment shown in FIG. 7, needle 26 can have a notch 33 communicating with the lumen of the needle to allow flashback blood to enter the flashback passage between the outer surface of the needle and the inner surface of the catheter 58. The catheter is configured so that the distal end of the catheter is constricted at 115 around the distal end of the needle and a gap or passage 117 is formed proximally of the constricted end to receive the blood passing through the notch where the blood is visible by the clinician.

The curves profile on the side surface 38 opposite the bevel 40 and the smaller diameter lumen enable the positioning of the tip 46 radially inward relative to the position of the tip 22 of needle 10. In one embodiment, the tip 46 is spaced radially inward from the peripheral outer surface of the body 26 a distance of about ¼ to about ⅓ the outer diameter of the body 26. In further embodiments, the tip 46 is spaced radially inward about ⅓ the outer diameter of the body 28. As shown in FIG. 3, the cutting edges 47 extend from the tip 46 and terminate at a point past or above the axial center line of the needle indicated by line 49 relative to the second longitudinal side surface 38. As shown, the distal end of the cutting edges are spaced from the center axis 49 on a side opposite the tip 40.

Figure 8:
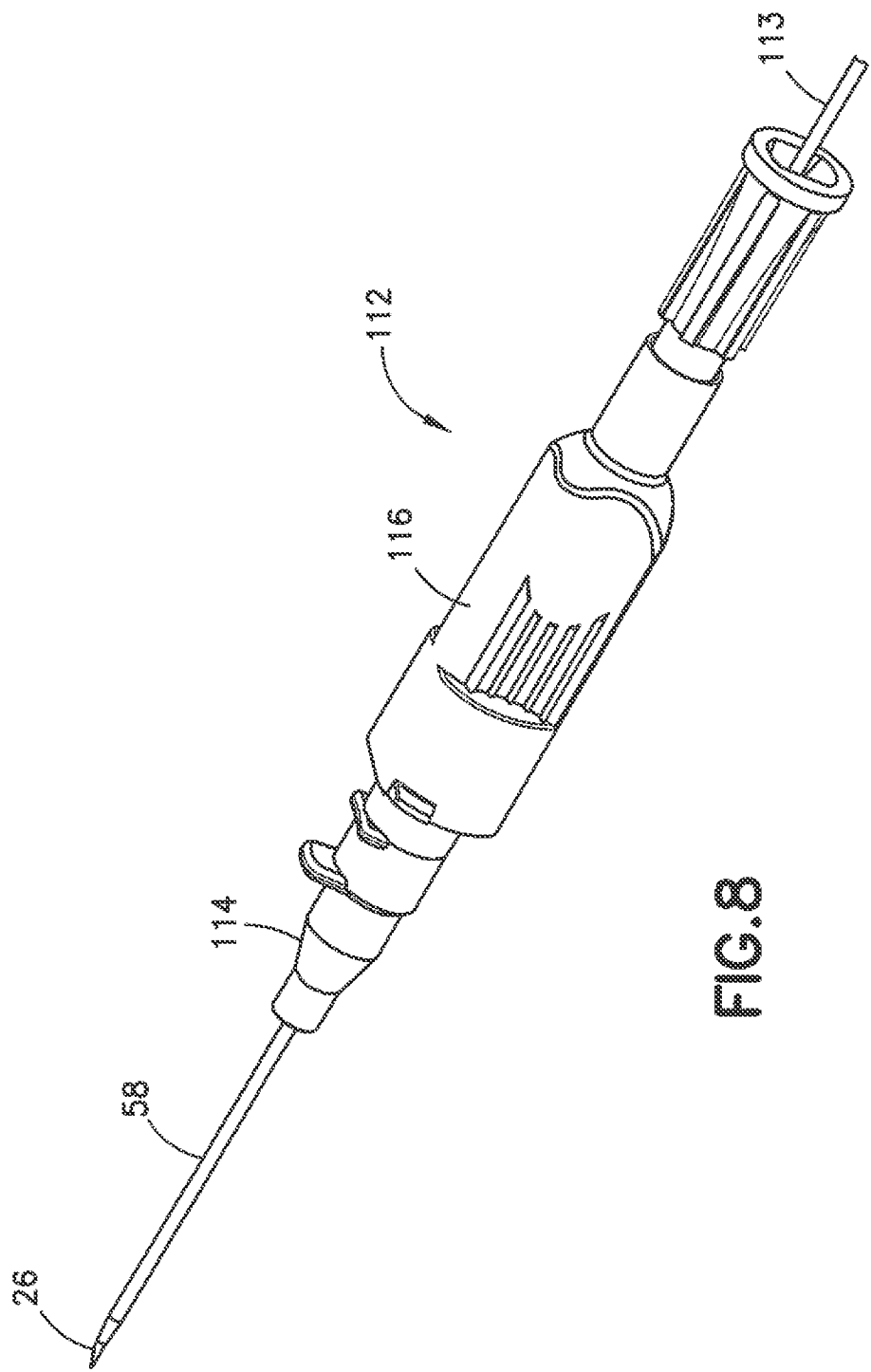
FIG. 8 is a perspective view of a catheter assembly in one embodiment of the invention.
Figure 10A:
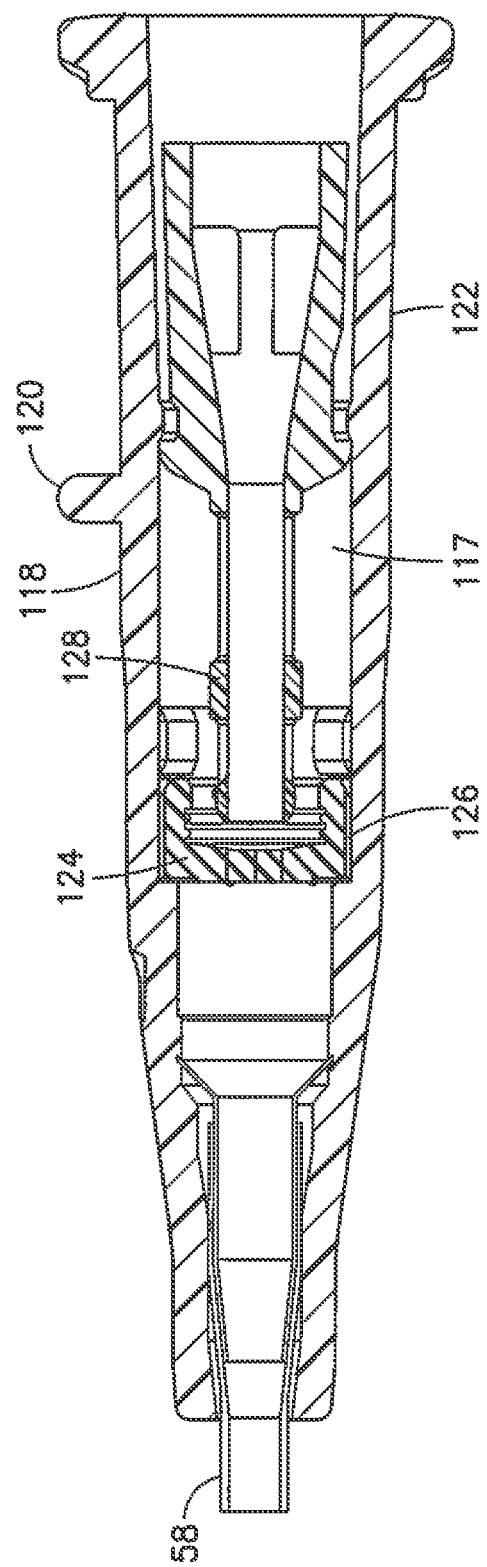
FIG. 10A is a partial cross sectional view of the catheter assembly of FIG. 8.
Figure 10B:
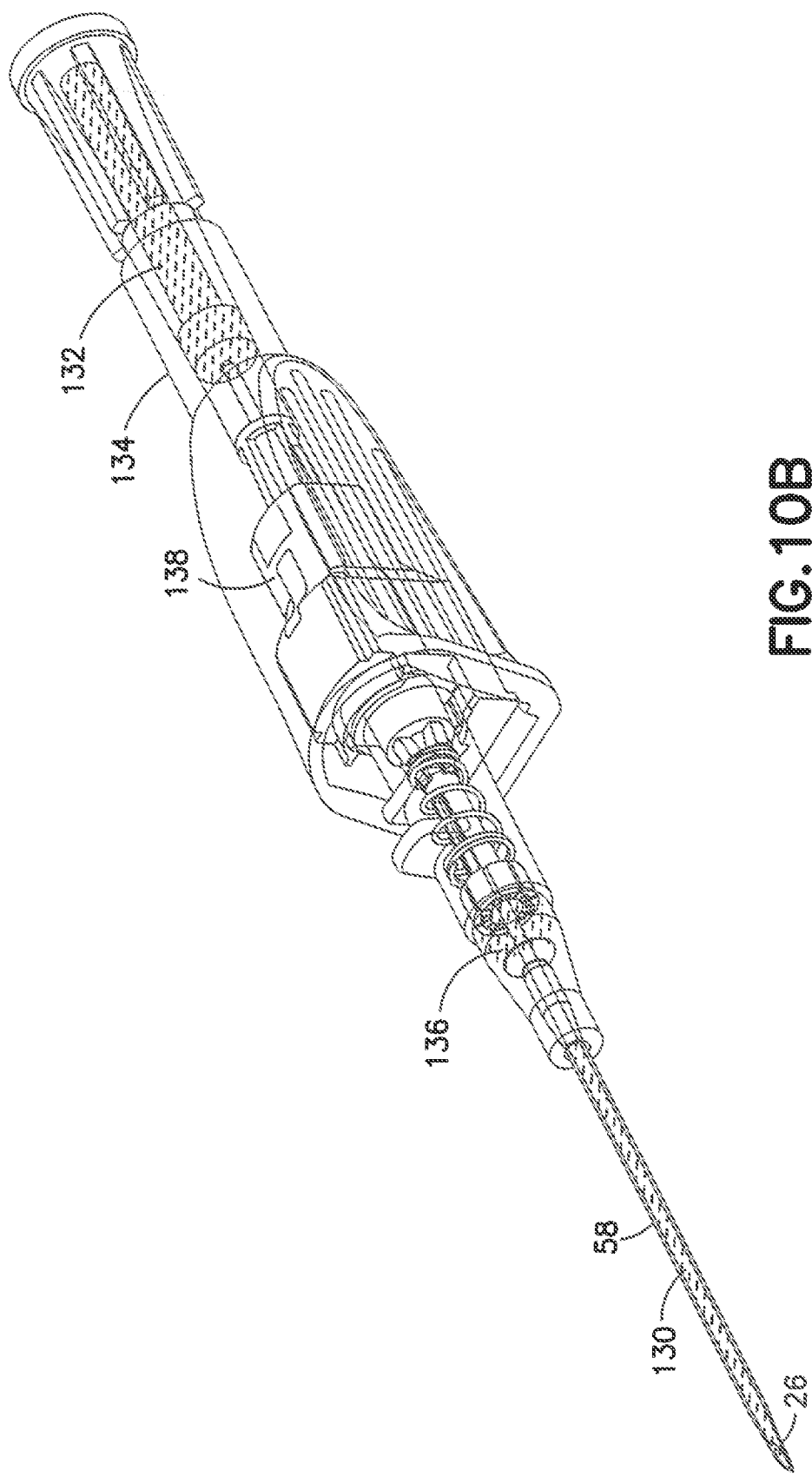
FIG. 10B is a perspective view of the catheter assembly of FIG. 8 showing the blood flashback.

Needle 26 can be used in a catheter assembly 112, as shown in FIGS. 8-10, and includes the hollow introducer needle 26, a catheter hub 114, and a needle hub 116. The needle 26 can have a sharpened distal end as shown in FIGS. 2 and 3 that extends through the catheter hub 114. An example of a catheter hub assembly having a blood flashback feature is disclosed in WO2015/161294, which is hereby incorporated by reference in its entirety. The flexible catheter 58 extends from the distal end of the catheter hub 114, with the needle 26 passing through the catheter 58. A guide wire 113 can be included in the catheter hub assembly to advance through the lumen of the needle into the vein for guiding the catheter into the vein. Initially, the needle 26 is inserted into a patient's vein. The catheter 58 is pushed along the needle 26 and into the vein following the needle 26. After the catheter 58 is inserted, the needle 26 is removed from the patient's vein and the catheter hub 114, leaving the catheter 58 in the patient as the needle 26 is discarded.

Catheter hub 114 has a distal end, a proximal end, and an outer surface. The distal end includes a catheter opening and the proximal end includes a Luer connector opening with projections for coupling with the Luer connector. A channel permits fluid passage through the catheter hub 114. The outer surface on a first longitudinal side surface 118 includes one or more projections 120, such as thumb or finger tabs, for manually manipulating the catheter hub 114 during insertion into the patient. The projections can be a thumb tab to assist the clinician in holding and manipulating the catheter assembly 112 during use. A second longitudinal side surface 122 opposite the first longitudinal side surface 118 in the embodiment shown is substantially flat to lie easily against the skin of the patient during use without interference from projections, tabs or the like. The catheter hub 114 may be made from a polymer material that is transparent or semi-transparent so that fluid flow through the catheter hub may be observed by a user or it may be made from an opaque material. In the embodiment shown, needle 26 is oriented where the cutting surface 48 and reverse bevels 42 and 44 face outwardly from second longitudinal side surface 118.

The flexible catheter 58 extends through the catheter opening and is secured to the catheter hub. A pre-slit resilient septum 124 is positioned in the channel to form a fluid-tight seal and selectively admits fluid to or from the flexible catheter 58. The septum selectively permits or blocks the flow of fluid through the flexible catheter 58.

The septum 124 includes a plurality of axial flow channels 126 on an outer circumference of the septum 124. The flow channels 126 have a width and depth so that when the septum 124 is not opened, blood can enter and air can escape the space distal of the septum 124 in the front portion of the catheter hub. At the same time, the flow channels 126 are sized small enough to prevent blood from exiting past the septum for a period of time. When the catheter 58 is initially inserted into a patient, and the introducer needle 26 is removed, the septum 124 prevents blood from flowing through the channel and out of the distal end. The septum 124 is made of an elastic material, such as a silicone rubber, to form the valve. Other elastic materials may be used and non-elastic materials may be incorporated in the septum 38 as needed.

An actuator 128 is positioned in the channel and is axially moveable in the channel to engage and open the slits of the septum 124. The actuator is a substantially tubular member with an internal passage to allow fluid to flow through the actuator 128 and through the septum 124 when the septum 124 is opened or penetrated by the actuator 128.

FIGS. 8-10A illustrate an exemplary embodiment of blood flashback features in the catheter assembly 112. Flashback is the visibility of blood that confirms the entry of the needle tip into the vein. Flashback indicated by reference number 130 in FIG. 10B is seen through the catheter 58 as blood travels into the open distal end of the hollow needle 26, out a notch or opening 33 in the needle 26 near the needle tip shown in FIG. 7, and up through the internal annular space between the needle 26 and the inside of the catheter 58. A second flashback 132 is seen in the needle hub/grip 134 forming a blood control member when blood comes out of the back of the needle 26 and enters a flash chamber in the needle hub/grip 134. Air is vented by a plug in the back of the needle hub/grip 134 by a porous membrane or micro grooves. A third flashback 136 is visible in the catheter hub 114 when the blood from the primary flashback flows into the catheter hub and stops at the blood control septum. A safety assembly 138 including a spring clip or locking mechanism is included to cover the tip of the needle 26 once the needle is withdrawn from the catheter to prevent accidental needle stick and prevent re-use of the needle. An examples of a needle protection member is disclosed in US 2017/0043134, which is incorporated by reference in its entirety.

In the embodiments shown in FIGS. 4-6 the catheter 58 is positioned on needle 10 and needle 26 where the needle functions as an introducer needle to position the catheter in the vein. The curved profile of the second longitudinal side forms sharp distal tip 46 of needle 26 that can penetrate the skin and the vein by orienting the needle at a steep first angle as shown in FIG. 4. The first angle of penetration can be about 55° to 65° and generally about 60° with respect to the surface of the skin and the longitudinal dimension of the vein. As the distal end of needle 26 pierces the vein and enters the lumen of the vein, the curved, comparatively smooth distal portion 54 can contact the inner surface of the vein as shown in FIG. 5 rather than sharp distal tip 46 to reduce the possibility of the sharp distal tip 46 penetrating the inner surface of the wall of the vein a location opposite the insertion site. The curved distal portion 54 promotes the insertion of the needle and catheter into the vein at a low angle as shown in FIG. 6 with a reduced risk of fixation or damage to the inner surface of the vein.

As shown in FIGS. 4 and 5, the needle 10 can penetrate the skin and vein where the tip 22 and the shorter cutting edge 24 can more easily contact the inner surface of the vein and result in injury to the inner surface of the vein at a location opposite the insertion site. The curve portion 54 of the needle 26 and the shorter axial length of the cutting edge 48 reduces the risk of injuring the inner surface of the vein by encouraging the shallow angle of the needle 26.

When the needle 26 is inserted into the vein in the position shown in FIG. 6, the distal end of the catheter 58 is positioned in the lumen 61 of the vein 60. The guide wire 113 can be advanced through the lumen of the needle 26 and the catheter 58 then can be advanced over the distal end of the needle 26 into the vein. Once the catheter is properly positioned in the vein, the guide wire and/or needle 26 can be withdrawn from the catheter 58 and the discarded. The curved profile 58 of the distal end of the needle 26 enables the catheter 58 to slide easily from the distal end of the needle 26 and bend over the distal end 54 into the vein with a lower incidence of damaging the inner surface of the catheter.

Figure 11:
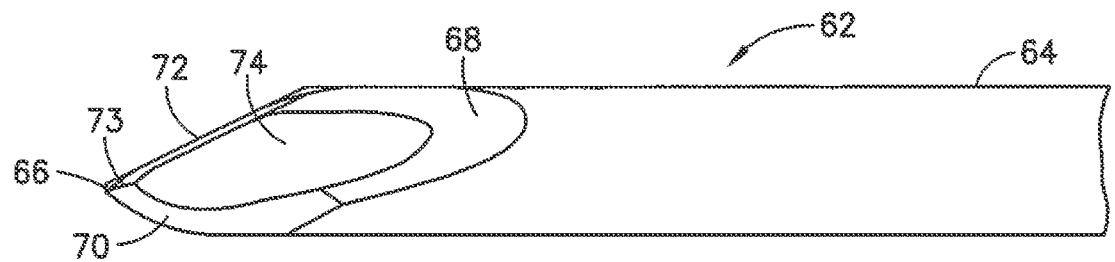
FIG. 11 is a perspective view of a needle having a beveled tip.
Figure 12:
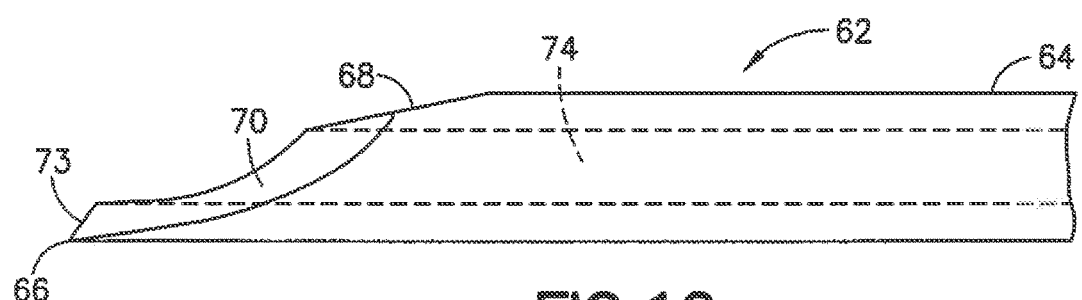
FIG. 12 is a side view of the needle of FIG. 11.

FIG. 11 and FIG. 12 show a needle 62 in a further embodiment having a body 64 with a distal end portion forming a sharp distal tip 66. The distal tip 66 is formed by a first bevel 68 formed at a first inclined angle and extending from the outer peripheral edge toward the distal tip 66. A second bevel 70 and a third bevel 72 extend from a distal end of the first bevel 68 to the distal tip 66 at a second angle that is steeper relative to the shallow angle of the first bevel 68. The second bevel 70 and the third bevel 72 converge to an inclined cutting edge 73 that has a steeper angle than the angle of the first bevel 68. In the embodiment shown, the second bevel 70 and third bevel 72 have an axial length greater than the axial length of the first bevel 68. A lumen 74 extends through needle and is formed by a substantially cylindrical inner surface. As shown in FIG. 12, the inner surface of the lumen 74 extends from the inner end of the cutting edge 73 in a straight line.

Figure 13:
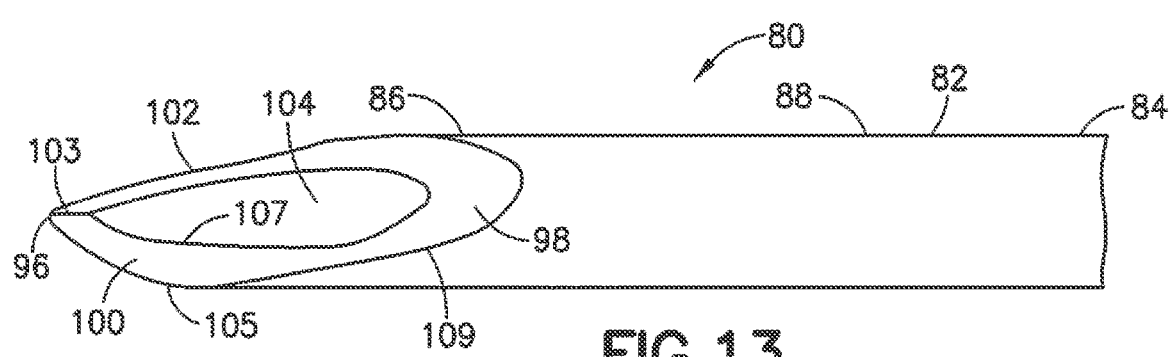
FIG. 13 is a perspective view of the needle according to a second embodiment of the invention.
Figure 14:
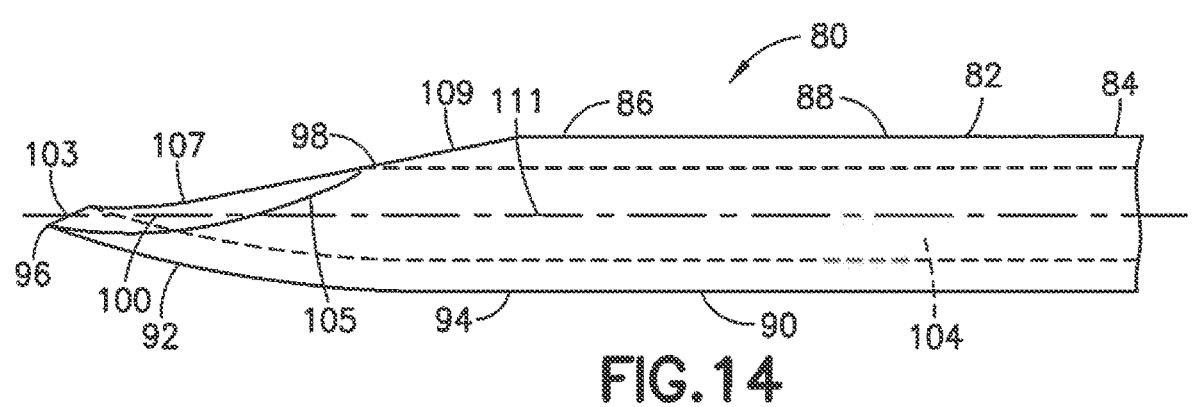
FIG. 14 is a side view of the needle of FIG. 13.

A further embodiment is shown in FIGS. 13 and 14 that includes a needle 80 having a longitudinal body 82 forming a needle shaft with a proximal end 84 and distal end 86. The body 82 has a cylindrical shape with a first longitudinal side surface 88 and a second longitudinal side surface 90 opposite the first longitudinal side surface 88. A distal portion 92 of the second longitudinal side surface 90 is formed with a continuous curved, convex profile as shown in FIG. 14 that curves from an outer peripheral edge 94 of the body 82 to a distal tip 96. As shown in FIG. 14, the needle 80 has a bevel 98 cut on the first longitudinal side surface 88 converging at distal tip 96. The first bevel 98 is formed on first longitudinal side 88 at a relatively shallow angle relative to the longitudinal dimension of the needle body and converges toward distal tip 96. In one embodiment, the bevel 98 can be cut at an angle of about 17-22° with respect to the longitudinal axis of the body 82. A second bevel 100 and a third bevel 102 are formed on first longitudinal side 88 and extend from a distal end of first bevel 98 and converge at distal tip 96 forming a cutting edge 103 at the juncture of the bevels 100 and 102. The bevels 100 and 102 can be cut at an angle of about 40-50° relative to the longitudinal axis of the body 82. In the embodiment shown, the second bevel 100 and the third bevel 102 have a concave surface forming a convex outer cutting edge 105 and a convex inner edge 107. The first bevel 98 can also be formed with a concave surface forming a generally convex outer cutting edge 109.

The distal end portion 92 on the second side 90 curves toward the center axis of needle body 82 to form the curved surface of the distal end 92. As shown in FIG. 14, curved distal end 92 curves inwardly toward the center axis of the needle compared to needle 62 so that distal tip 96 is spaced radially inward of the outer peripheral surface of the body 82 with respect to the longitudinal axis. The distal tip 96 projects into the passageway formed by the inner surface of the lumen 104 of the body 82. The inner surface of the lumen 104 at the second side 90 curves inwardly with the curvature of the outer surface of the curved profile of the distal end 92 where the inner end of the cutting edge 103 projects into the passage defined by the lumen 104. As shown, the cutting edge 103 formed by the bevels 100 and 102 is spaced inwardly from the outer surface of the body. In the embodiment shown, the distal end of the cutting edges 103 is substantially aligned with the center axis of the lumen 104 indicated by line 111. The wall of body 86 is substantially uniform thickness so that the inner surface of the wall curves inwardly as shown in FIG. 14.

FIG. 15 shows a comparison of the bevel length and curved distal end portion 92 of needle 80 with the configuration of needle 62. The difference between the bevel length of needle 62 and needle 80 is indicated by line 81. The curvature of distal end portion 92 reduces the surface area of the inner edge 107 of the beveled surfaces 100, 102 to reduce the incidence of coring of the tissue during insertion into the vein compared to the open end of needle 62. The diameter of the open portion of the lumen 74 of needle 62 formed by the bevel is indicated by line 83. The diameter of the open portion of the lumen 104 formed by the bevels 70, 72 is indicated by line 85, which is smaller than the open portion of needle 62 by the tip and curved portion 92 curving radially inward with respect to the center axis of the needle 80. The diameter of the open end of the lumen 104 indicated by line 85 is smaller than the inner diameter of the lumen 104 in the body 82. FIG. 16 shows the needle with a notch 83 for flashback blood to pass between the needle and the catheter 58. As shown, the notch 83 is an opening to the lumen 104 that is spaced from the distal end. In another embodiment, needle body 82 can be a solid body without a lumen to avoid tissue coring. The solid needle body typically includes a groove, recess or other blood passage to form a blood flashback passage.

Needle 80 can be connected to a catheter assembly 112 and blood flashback member as in FIGS. 8-10A for use in positioning the catheter 58 in the vein 104 shown in FIGS. 17 and 18. In the embodiment of FIGS. 17 and 18, the needle 80 is oriented with respect to the catheter hub and needle hub where the curved surface 92 of the second longitudinal side of the needle 80 faces outwardly from the second longitudinal side surface of the catheter hub. FIGS. 17 and 18 show the orientation of the needle 80 of FIG. 13 during insertion to a vein 104 where the needle is oriented with the curved distal end portion 92 facing the outer surface of the skin and vein with respect to the point of entry and insertion site in the patient. The curved distal portion 92 provides a surface that when contacting the inner surface 105 of the vein 104 reduces the risk of damage or fixation of the vein during the insertion step. FIG. 17 shows the curved distal portion of the needle promoting the shallow angle of the needle during insertion to properly position the needle and/or catheter in the vein with a reduced risk of damage to the inner surface of the vein. The shorter axial length of the cutting edges of the needle tip enables a faster cutting action for a predetermined insertion rate that reduces the perceived pain to the patient. FIG. 18 shown the needle 80 at the shallow angle after insertion into the vein 104 and the catheter 58 advanced over the needle 80 into the vein. In other embodiments, a guide ware can be passed through the lumen of the needle 80 to portion the catheter in the vein. The guide wire and needle can then be removed on the catheter is properly positioned.

FIG. 19 illustrates an alternative method for inserting the needle 80 into the vein 104 of the patient by orienting the needle where the curved distal surface faces away from the surface of the skin and the vein 104 during insertion. The curvature of the distal end of the needle as shown in FIG. 18 promotes a flattening of the angle of the needle during insertion after the initial insertion angle to assist in positioning the needle and catheter in the vein 104 with a reduced risk of damage to the inner surface 105 of the vein at a location opposite the insertion site.

An example of a flashback feature formed in the needle is shown in FIGS. 20 and 21 where the first longitudinal surface of the needle is crushed or crimped to form a substantially V-shaped groove or recess 110. In the embodiment of FIG. 20 the wall of the needle is crimped in a manner to form a protruding portion 112 extending into the axial passage of the needle. The protruding portion forms a surface to reduce the inner diameter of the needle to reduce the incidence of coring during insertion into the skirt and vein of the patient. FIGS. 21 and 22 show an alternative configuration where the inner edge of the open end of the needle is formed with a rounded edge 114 to reduce the coring of the tissue during insertion.

The above description of the preferred embodiments is not to be deemed as limiting the invention, which is defined by the appended claims. The disclosure is intended to enable the artisan of ordinary skill to practice variants of the invention described without departing from the scope of the invention. Numerical limitations herein, in the specification and in the claims, are understood to be limited by the modifier "about," such that minor departures yielding equivalent results is within the scope of the invention. Features or dependent claim limitations disclosed in connection with one embodiment or independent claim may be combined in another embodiment or with, a different independent claim without departing from the scope of the invention.

What is claimed is:

1. A needle comprising:
a body having a longitudinal dimension with a proximal end and a distal end; a lumen extending between said proximal end and said distal end, a first longitudinal side surface, a second longitudinal side surface opposite said first longitudinal side surface;
a first bevel surface extending at an angle of about 12-22° with respect to the longitudinal dimension from said first longitudinal side surface to said second longitudinal side surface to form a distal tip, a second reverse bevel surface and a third reverse bevel surface on a peripheral surface at said second longitudinal side surface and converging to said distal tip and said first bevel surface, said second reverse bevel surface and third reverse bevel surface being oriented relative to said first bevel surface to define a first cutting edge between said second reverse bevel surface and said first bevel surface, and a second cutting edge between said third reverse bevel surface and said first bevel surface, where a length of said first cutting edge between said second reverse bevel surface and said first bevel surface and a length of said second cutting edge between said third reverse bevel surface and said first bevel surface is about ⅓ to ½ a length of said first bevel surface, and said first cutting edge and said second cutting edge oriented at an angle of about 75-85° with respect to each other; and
a curved distal end surface at a distal end of said second longitudinal side surface of said body, said curved distal end surface extending from an outer peripheral surface of said second longitudinal side surface toward said distal tip of said body, and where said distal tip is oriented radially inward from said first and second longitudinal side surface, and said second reverse bevel surface and third reverse bevel surface converging to define a longitudinally extending distal cutting edge extending from said distal tip to said curved surface on said second longitudinal side surface of said body, said distal cutting edge oriented at an angle relative to the longitudinal dimension of said body, and wherein said curved distal end surface forms a continuous curvature with said distal cutting edge extending between said outer peripheral surface and said distal tip, and where said distal cutting edge faces radially outward from said curved distal end surface, and said distal cutting edge defined by said second reverse bevel surface and third reverse bevel surface has a curved profile and a distal end at said distal tip, and a ratio of a length of said distal cutting edge between said second reverse bevel surface and third reverse bevel surface to the axial length of said first bevel surface is 1:2.5 to 1:3.

2. The needle of claim 1, wherein said second and third reverse bevel surfaces have a longitudinal length of one half of a longitudinal length of said first bevel surface.

3. The needle of claim 1, wherein said lumen has an inner diameter not more than about ⅓ a radial dimension of an outer side wall of said body at said distal end.

4. The needle of claim 3, wherein said lumen has an open distal end oriented between said distal tip and said first longitudinal surface of said cylindrical body.

5. The needle of claim 1, wherein said distal tip and said distal cutting edge formed between said second and third bevel surfaces are spaced radially inwardly from said outer peripheral surface and radially inwardly from an inner surface of said lumen.

6. The needle of claim 1, wherein a ratio of an axial length of said second reverse bevel surface and said third reverse bevel surface to an axial length of said first bevel surface is 1:1.5 to 1:1.8.

* * * * *